United States Patent [19]

Bohon et al.

[11] Patent Number: 5,461,313
[45] Date of Patent: Oct. 24, 1995

[54] METHOD OF DETECTING CRACKS BY MEASURING EDDY CURRENT DECAY RATE

[75] Inventors: William M. Bohon, Anchorage, Ak.; Pedro F. Lara, Dallas, Tex.

[73] Assignee: Atlantic Richfield Company, Los Angeles, Calif.

[21] Appl. No.: 80,360

[22] Filed: Jun. 21, 1993

[51] Int. Cl.⁶ .......................... G01N 27/90; G01N 27/72; G01N 27/82
[52] U.S. Cl. .............. 324/240; 324/227; 324/243
[58] Field of Search .............. 324/207.16, 207.17, 324/209, 220, 221, 222, 227, 228, 229, 239, 240, 243

[56] References Cited

U.S. PATENT DOCUMENTS

| | | | |
|---|---|---|---|
| 2,965,840 | 12/1960 | Renken, Jr. et al. | 324/240 X |
| 3,090,910 | 5/1963 | Moran | 324/221 X |
| 4,602,212 | 7/1986 | Hiroshima et al. | 324/240 X |
| 4,769,598 | 9/1988 | Krieg et al. | 324/219 |
| 4,839,593 | 6/1989 | Spies | 324/240 |
| 4,843,319 | 6/1989 | Larn | 324/240 |
| 4,843,320 | 6/1989 | Spies | 324/240 |
| 5,233,297 | 8/1993 | Lara | 324/229 X |

*Primary Examiner*—Sandra L. O'Shea
*Assistant Examiner*—Roger C. Phillips
*Attorney, Agent, or Firm*—Geoffrey A. Mantooth

[57] ABSTRACT

There is provided a transient electromagnetic method and apparatus for inspecting objects. The apparatus includes a sensing portion, which has a transmitting antenna and at least one receiving antenna thereon. The sensing portion is located adjacent to the object which is to be inspected such that the antennas are adjacent to the object. There is also a magnet located adjacent to the sensing portion. The magnet has poles located adjacent to the object, so as to provide a steady-state magnetic field to the object. By inducing eddy currents into the object, families of cracks, such as caused by environmental conditions, can be detected. In addition, magnetic flux leakage methods can be used in combination with the transient electromagnetic method to further assisting detecting crack families in pipeline inspection applications.

6 Claims, 5 Drawing Sheets

METHOD OF DETECTING CRACKS BY MEASURING EDDY CURRENT DECAY RATE

FIELD OF THE INVENTION

The present invention relates to electromagnetic diffusion methods for non-destructively inspecting objects, such as pipelines, tubing, storage tanks, etc., for cracks.

BACKGROUND OF THE INVENTION

Piping and vessels are subjected to environmental cracking over their useful service life. Environmental cracking is caused by a reaction between the alloy or steel used to make up the piping or vessel and the local environment, with the pipe or vessel under stress. Environmental cracking is different than fatigue cracking, which is caused solely by cyclical mechanical loading. Environmental cracking can occur at much lower levels of stress than fatigue cracking. Some types of environmental cracking include stress corrosion cracking, sulfide stress cracking and hydrogen induced cracking.

Environmental cracking is a concern because it can cause catastrophic equipment failure, resulting in damage to the environment, loss of life and loss of production from the equipment. As an example, stress corrosion cracking has been responsible for numerous pipeline failures. Thus, there is a need to develop non-destructive techniques that will detect areas of a pipe or vessel that have been subjected to environmental cracking. Such detection would permit corrective measures to be taken to prevent catastrophic equipment failure.

Environmental cracking is difficult to detect with conventional non-destructive techniques. Some techniques, such as magnetic particle testing and dye penetrant testing, are capable of detecting environmental cracking, but only with direct access to the wall of the piping or vessel. However, many testing situations exist where direct access to the wall is not possible. For example, direct access is not possible when searching for stress corrosion cracking on the exterior surface of a buried pipeline. Nor is direct access possible when searching for sulfide stress cracking on the interior surface of a vessel that is still in service.

Some conventional non-destructive testing techniques do not require direct access to the cracked surface. However, these techniques are not effective in detecting environmental cracking. For example, stress corrosion cracks are typically compact and filled with corrosion products. It is believed that this makes detection difficult with conventional shear wave (or angle beam) ultrasonic testing or with radiographic testing. In addition, stress corrosion cracking in pipelines is oriented longitudinally. This makes the stress corrosion cracking undetectable with magnetic flux leakage testing that is implemented with in-line inspection pigs, because the magnetic field lines run parallel to the cracks.

SUMMARY OF THE INVENTION

It is an object of the present invention to provide a method for detecting environmental cracking in piping and vessels without relying on direct access to the cracked surface.

The method of the present invention detects cracks in an electrically conductive object. The method induces an eddy current into a portion of the object using an abruptly changing magnetic field. While the induced eddy current decays in the object portion, the rate of decay of the induced eddy current is detected. The abrupt change in the rate of detected decay is used to determine if a family of cracks is present in the object portion.

The present invention allows the detection of environmental cracking without direct access to the object under test. Such cracks have been difficult to detect in situations were direct access is denied by the installation circumstances of the object. With the present invention, the inspection apparatus can be located on one side of a conductive object and detect cracks on the other side of the object.

In one aspect of the present invention, the step of determining if a family of cracks is present in the object portion from the detected decay further includes the step of distinguishing between a family of cracks in the object portion and the reduction in thickness of the object portion by determining the magnetic flux leakage of the object portion.

DESCRIPTION OF PREFERRED EMBODIMENT

The present invention uses transient electromagnetic techniques to detect environmental cracking in general. The present invention is especially useful in detecting stress corrosion cracking, which typically produces families of cracks that extend longitudinally along a pipeline. The preferred embodiment will be described in the context of detecting cracks in or on pipelines. However, the present invention can be used to detect cracks in other situations, such as in vessels and the like.

Use of transient electromagnetic methods and apparatuses are shown and described in U.S. Pat. Nos. 4,843,319, 4,843,320 and 4,839,593, and U.S. Pat. No. 5,233,297 the disclosures of which are incorporated herein by reference.

Figure 1:
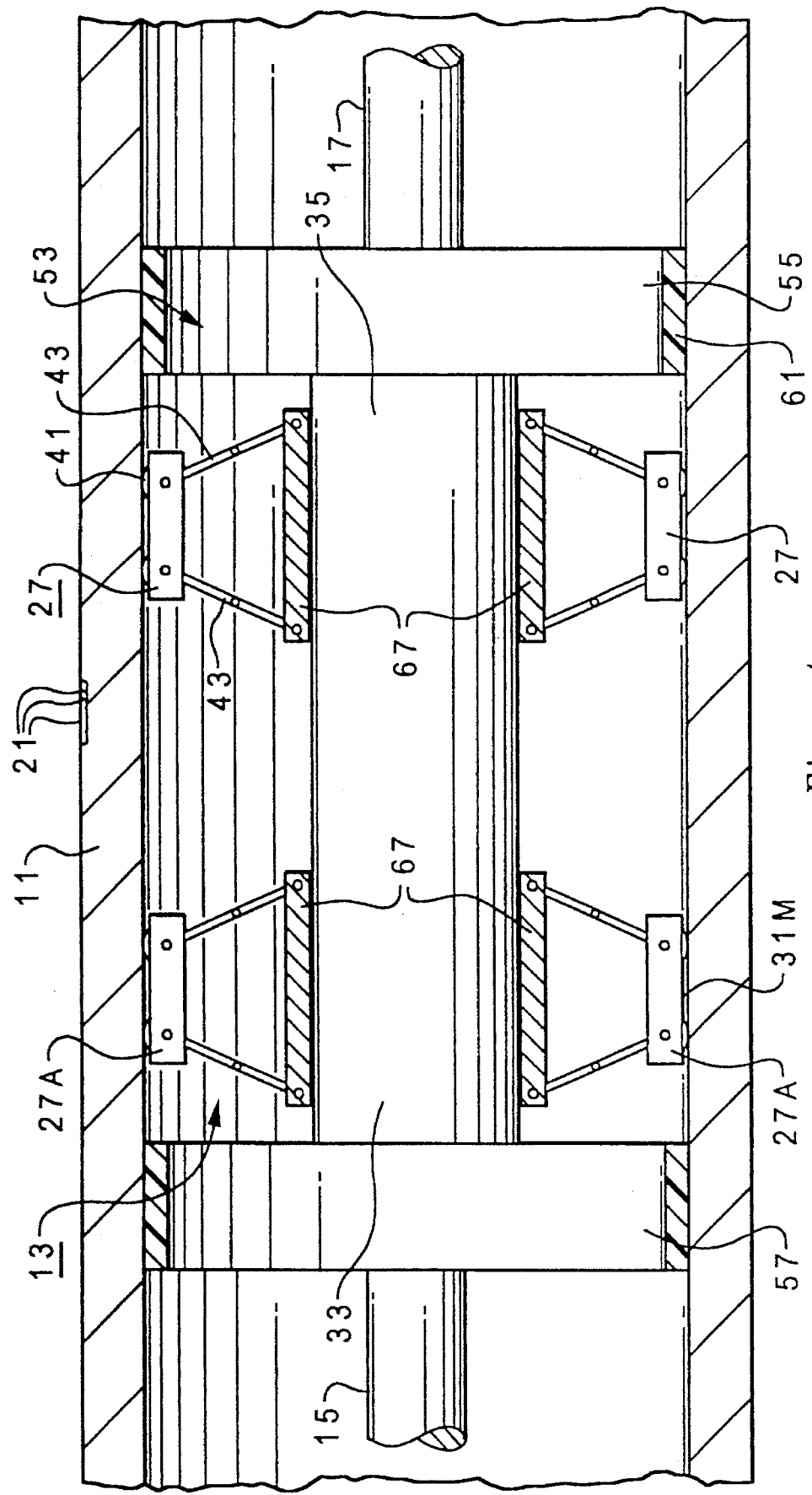
FIG. 1 is a side view of a testing apparatus that is used to practice the method of the present invention, in accordance with a preferred embodiment.

In FIG. 1, there is shown a testing apparatus 13 for carrying out the method of the present invention. The testing apparatus is located inside of a pipeline 11 and has pig attachments (not shown) on both ends 15, 17 to facilitate its movement through the interior of the pipeline.

The testing apparatus 13 includes plural sensing heads 27, downhole electronics 33, and a body member 35.

Figure 2:
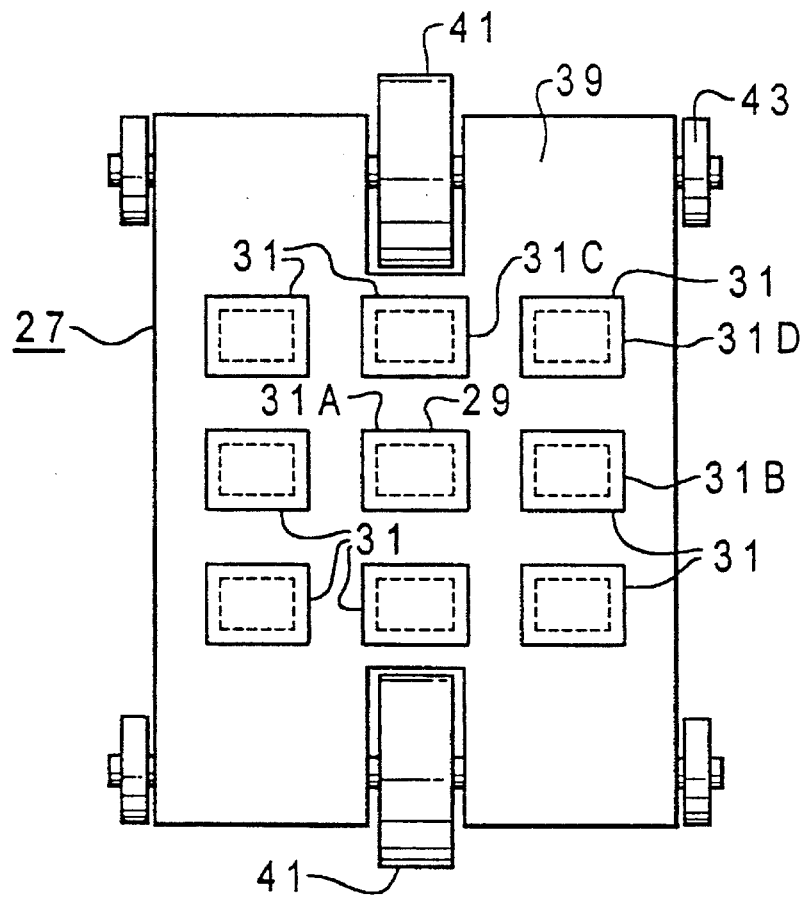
FIG. 2 is a front or plan view of a sensor head assembly.

Referring to FIGS. 1 and 2, the sensing heads 27 each contain transmitting and receiving antennas 29, 31. There may be provided plural sensing heads 27, wherein the sensing heads 27 are disposed around the circumference of the testing apparatus 13 and are large enough to provide 360 degrees circumferential coverage of the pipe wall. To prevent contact between adjacent sensing heads, the sensing heads 27 are longitudinally displaced from each other along the body member 35. Thus, there is a forward (relative to the direction of travel of the apparatus) pair of sensing heads and a rear pair of sensing heads. Each pair has two diametrically opposed sensing heads. The rear pair is rotated 90 degrees from the forward pair to provide for complete circumferential coverage. Each sensing head has an arcuately shaped outer surface 39 (see FIG. 2) that approximately corresponds to the curvature of the inside surface of the pipe 11. Each sensing head 27 has a pair of rollers 41 thereon for contact with the casing 11. The rollers 41 protect the antennas 29, 31 from abrasion with the pipeline wall 11. It is preferred to locate the antennas as close as possible to the wall in order to increase resolution. As an alternative to rollers, materials that perform well under abrasion are available for use. Each sensing head 27 is mounted onto the body member 35 by a pair of arms 43. The arms 43, which are spring loaded, force the sensing head into rolling contact with the inside surface of the pipe.

Figure 3:
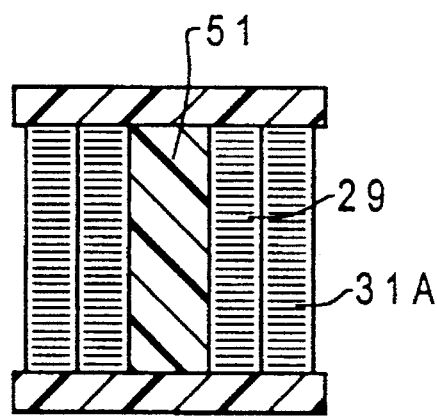
FIG. 3 is a cross-sectional view of the transmitting and receiving coil arrangement.
Figure 4:
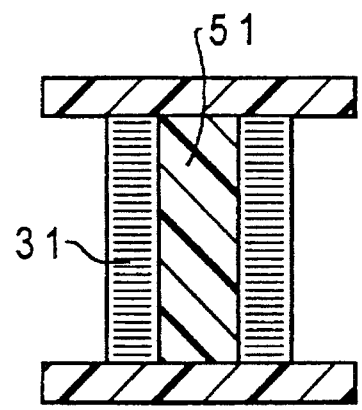
FIG. 4 is a cross-sectional view of a receiving coil arrangement.

Each sensing head 27 (see FIG. 2) has plural antennas located thereon so as to be adjacent to the piping wall. In the center of each sensing head 27 is a transmitting antenna 29 and a coincident receiving antenna 31A. Both transmitting and receiving antennas 29, 31A are wound onto the same core 51, as shown in FIG. 3. The core 51, which is in the shape of a spool, is made of a non-magnetic and non-conductive material such as plastic. The respective antennas are made up of respective coils of wire. There are also provided plural receiving antennas located around the central transmitting antenna 29. Each receiving antenna 31 is made up of a coil of wire wrapped onto a core 51 (see FIG. 4). The antennas are oriented in the sensing head 27 so that the longitudinal axes of the cores 51 are perpendicular to the adjacent portion of casing walls. In addition, receiving antennas having their longitudinal axes are oriented so as to be parallel to the adjacent wall are provided. Thus, at each receiving antenna location, there are two receiving antennas, with one being oriented perpendicular to the wall and the other being oriented parallel to the wall.

The receiving antennas 31 other than the coincident antenna 31A are placed in various spatial orientations with respect to the transmitting antenna 29. Thus, there are receiving antennas 31B that are located laterally or transversely from the transmitting antenna 29. The transverse antennas 31B are located along a first imaginary line extending between the respective transverse antenna and the transmitting antenna 29, which first imaginary line is perpendicular to the direction of motion of the transmitting antenna. There are also receiving antennas 31C that are located longitudinally from the transmitting antenna 29. The longitudinal antennas 31C are located along a second imaginary line extending between the respective longitudinal antenna and the transmitting antenna 29, which second imaginary line is parallel to the direction of motion of the transmitting antenna. And there are receiving antennas 31D that are located both transversely and longitudinally (diagonally) from the transmitting antenna 29.

The sensing heads 27 are coupled to a collar 67 that is coupled to the body member 35.

The testing apparatus 13 may be equipped with a magnet to increase the speed of inspection of the pipeline wall. It is believed that the magnetic field reduces the ferromagnetism of the pipe wall by aligning the magnetic domains of the wall along the path of the magnetic field. As the ferromagnetism of the pipe wall decreases, the penetration and diffusion speeds of the eddy currents induced by the transmitting antenna 29 increases. This is because the induced eddy currents do not interact with the aligned magnetic domains of the pipe wall. Faster penetration times allow faster inspection speeds. Thus, the testing apparatus 13 can be moved along inside of the pipe at a faster speed when inspecting with the magnetic field. In addition, faster diffusion speeds increase the resolution of inspection by limiting the spatial diffusion of the induced eddy currents. Thus, the eddy currents are focused more into a narrow cone within the pipe wall. When the magnetic field is strong, for example, greater than 20,000 gauss, the material in a pipe wall has even been observed to act paramagnetically. Thus, in paramagnetic conductors, eddy current diffusion speeds are maximum, tool resolution is maximum, and focusing of the eddy currents is maximum, wherein cracks can be detected in paramagnetic conductors.

The steady-state magnetic field produced by the magnet is strong enough to saturate the wall with the dc magnetic field. For example, the dc magnetic field could be 1000 gauss.

Referring to FIG. 1, the sensing heads 27 are located between the poles of a magnet 53. In the preferred embodiment, the magnet is a permanent magnet. The magnet 53 has a first pole piece 55 and a second pole piece 57. The pole pieces 55, 57, which are disc shaped, extend radially outward from the body member 35. The outside of the body member physically and magnetically couples the pole pieces together. The pole pieces and the outside of the body member are made up of a material (such as iron) that is high in magnetic permeability so as to allow for a magnetic field. The pole pieces 55, 57 are sized so as to have a diameter that is slightly smaller than the inside diameter of the pipe 11. Plastic end pieces 61 can be provided in the gap between the pole pieces and the pipe wall so as to reduce wear caused by contact between the pole pieces and the pipe wall. The magnetic permeability of the gap is enhanced by mixing iron powder with the plastic to form the pieces 61. For example, the composition of the pieces 61 could be 50% or more of iron powder. Alternatively, wire brushes could be used in the gap between the pole pieces and the pipe wall.

The magnet 53 need not be a permanent magnet. It could be some type of temporary magnet. If a temporary magnet, such as an electromagnet, is used, then appropriate connections to a power supply are provided. Use of a permanent magnet eliminates the need for a power supply. If need be, plural magnets could be used to obtain stronger magnetic fields.

In addition, plural magnets can be provided, with each magnet arranged in a unique orientation so as to provide steady-state magnetic fields in plural directional components. The use of magnetic fields in plural directions more fully saturates the object being inspected. It is preferable to provide steady-state magnetic fields in two orthogonal components. For example, the magnet 53 shown in FIG. 1 creates a magnetic field that is oriented longitudinally along the length of the pipe 11. A second magnet could be provided so as to create a magnetic field that is oriented circumferentially around the pipe. Such a magnet would have two poles positioned 180 degrees apart around the circumference of the testing apparatus 13. Thus, the poles would have a positioning arrangement similar to the two sensing heads 27 shown in FIG. 1.

Figure 5:
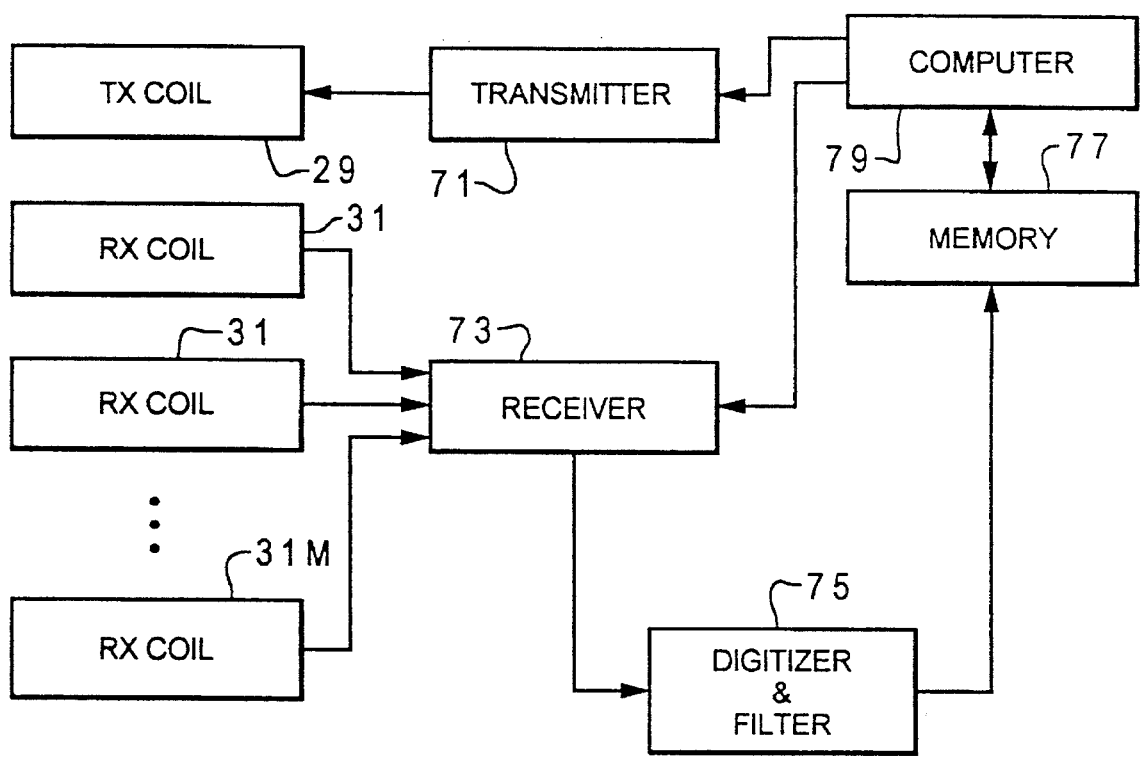
FIG. 5 is a block diagram of the electronics.

In FIG. 5, there is shown the transmitting and receiving antennas, that are contained in a sensing head, as connected to the electronics 33. The electronics 33 are located in the body member 35. The transmitting antenna 29 in each sensing head 27 is connected to a transmitter 71. The transmitter 71 generates a pulse having abrupt fall times on the order of 1–100 microseconds. Typically, the pulse has amplitudes of one to two amps. The pulses of the transmitter pulse train alternate polarity to eliminate dc bias in the instrumentation. Thus, the first pulse is positive, the second pulse is negative, the third pulse is positive, the fourth pulse is negative and so on. The duration of each pulse is sufficiently long to stabilize the pulse magnitude so that there are no currents induced into the casing wall before the occurrence of the abrupt fall time of the pulse.

The respective receiving antennas 31 of each sensing head 27 are connected to a receiver 73. The receiver 73 is a multi-channel instrument, having a channel for each receiving antenna. The receiver 73 is a broad-band instrument with a wide (5 or 6 orders of magnitude) dynamic range. An analog-to-digital converter 75 digitizes the data from each receiving antenna. The digitized data is filtered for 60 Hz noise rejection and sent to a memory 77 for storage until the logging apparatus 13 can be retrieved and the memory accessed.

The electronics 33 may contain as many transmitters and receivers as required. In the preferred embodiment, there are four transmitting antennas 29, one for each sensing head 27. One transmitter may energize all four transmitting antennas; either simultaneously or sequentially, or plural transmitters may be used. Likewise, plural receivers may be used, to provide an appropriate number of receiver channels. An appropriate number of digitizers 75 is also provided. A computer 79 is connected to the transmitter 71 and the receiver 73. The computer 79 coordinates data acquisition by the sensing heads by controlling the transmitter 71 and the receiver 73.

The method of inspecting the wall of the pipe 11 will now be described, referring to FIGS. 1–5. The testing apparatus 13, with pig attachments fitted thereon, is located within the pipeline 11. The magnet 53 produces a magnetic field in the pipe wall. The magnetic field is produced in the first pole piece 55, across the gap between the first pole piece and the wall, in the wall 19, across the gap between the second pole piece, in the second pole piece 57 and in the core that makes up the outside of the body member 35.

Next, the testing apparatus 13 is moved inside of the pipe. With the testing apparatus located inside of the pipe, the rollers 41 of the sensing heads 27 contact the inside surface of the pipe wall and the pole pieces 55, 57 of the magnet 53 are in close proximity to the pipe wall. The sensing heads 27 are forced into rolling contact with the pipe wall by the arms 43 such that there is a gap between the transmitting and receiving antennas and the pipe wall. The transmitting and receiving antennas on the sensing head are maintained at a relatively constant distance from the pipe wall.

As the testing apparatus 13 is moved along inside of the pipe, the transmitting antenna 29 on each sensing head 27 is energized by the transmitter 71. Each transmitting antenna 29 is energized for a sufficient length of time to stabilize the current in the antenna, thereby insuring no currents are induced into the wall 11. Then, each transmitting antenna 29 is abruptly deenergized by the transmitter, so that the current in the transmitting antenna rapidly falls to zero magnitude. This abrupt deenergization of the transmitting antenna induces current into that portion of the wall 11 that is adjacent to the respective transmitting antenna.

The induced eddy currents diffuse into the pipe wall. The presence of cracks 21 (see FIG. 1) in the pipe wall disrupts the diffusion of eddy currents and affects the decay. This disruption is detected from the decay. In FIG. 1, the cracks 21 are longitudinally oriented along the pipe and are located on the outside surface of the pipe. The plural cracks 21 are a family of stress corrosion cracks.

As soon as the respective transmitting antenna is deenergized, the receiver 73 (FIG. 5) that is associated with the adjacent receiving antennas 31 is switched on. The respective receiving antennas 31 detect the presence of and the decay of the induced current in the casing wall and produce a respective received signal representing the induced current. The received signals are received by the receiver 73, where they are amplified and filtered, and then digitized by the digitizer 75. The received signals are then stored in the memory 77. After the testing apparatus 13 is removed from the pipe, the memory 77 is accessed and the received signals are recovered and processed. Alternatively, the computer 79 could process the received signals to obtain a measurement of wall thickness as described in U.S. Pat. Nos. 4,843,319, 4,843,320 and 4,839,593.

Processing of the received signals is as described in U.S. Pat. No. 4,843,319 and U.S. Pat. No. 5,233,297, the disclosures of which have been incorporated herein by reference. The data from a received signal obtained from a receiving antenna 31 is normalized by taking the absolute value and then the logarithmic derivative. The wall thickness (either in quantitative or in qualitative terms) at a particular location is then obtained either by applying an empirically derived relationship or by comparing the derivatives with reference derivatives. For coincident or far fields the empirical relationship is as follows:

$$th = (d(\ln V)/d(\ln t) + 2.17 \ln t - b)/c$$

where th is the wall thickness, V is the voltage as measured by the respective receiving antenna, and t is time. The relationship is derived from a linear interpolation algorithm and as such b and c are interpolation constants. The relationship is applicable at intermediate-to-late times of a received signal, after the occurrence of a break point. The factors b and c are empirically derived and are dependent on diameter (in the case of pipes), wall thickness, metallurgy and temperature. Alternatively, the data can be compared to reference derivatives obtained from walls of known thickness, metallurgy and geometry and obtained with similar antenna geometries. Interpolation may be necessary to determine wall thickness.

Figure 6:
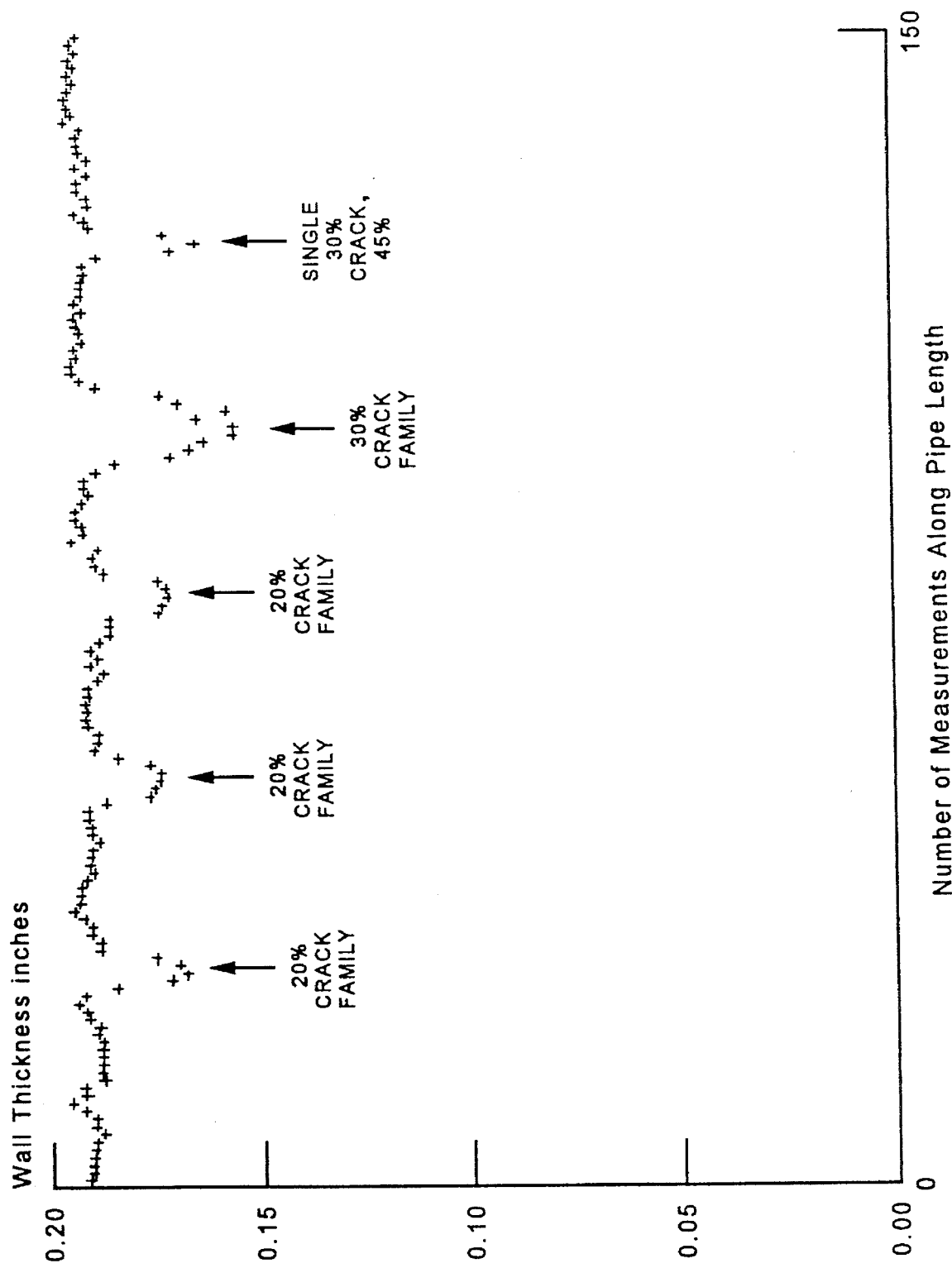
FIG. 6 is a graph showing a survey along a length of pipe that has families of cracks, performed using the method of the present invention.

The wall thickness measurements may then be plotted with reference to their location on the wall. For example, in FIG. 6, there is shown a wall thickness plot along the length of one section of a two inch pipe. The data was obtained using transmitting and receiving antennas moving inside the pipe and taking 150 measurements along the length of the pipe. The antennas were configured in a side-pitch-catch arrangement, wherein the receiving antenna 31B was oriented circumferentially and to the side (relative to the direction of travel) of the transmitting antenna 29. The antennas were separated by one inch. Five different anomalies in the wall thickness are shown in FIG. 6. The anomalies were machined on the exterior surface of the wall. The sensors moved along the interior surface of the wall. From left to right in FIG. 6, there were three crack families machined to a depth of 20% into the wall, a crack family machined to a depth of 30% into the wall and a single crack machined to a depth of 20% into the wall. Each family of cracks included three parallel slots oriented longitudinally and separated by ⅛ inch. The single crack was oriented at 45 degrees. Each crack was 0.008 inches in width.

All of the crack families were detected. Normal wall thickness for the pipe was 0.19 inches. The crack families with 20% depths were detected as having a remaining wall thickness of about 0.17 inches. The crack family with a depth of about 30% was detected as having a lesser remaining wall thickness. Two single cracks, one oriented longitudinally and the other circumferentially, went undetected.

Figure 7A:
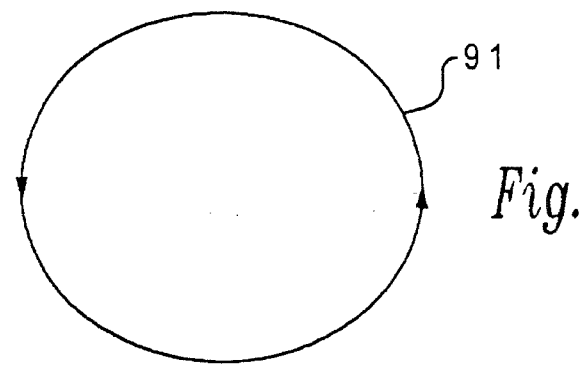
FIGS. 7a–7c are schematic representations showing eddy current patterns in walls with no cracks (FIG. 7a), with a single crack (FIG. 7b) and with plural cracks (FIG. 7c).
Figure 7B:
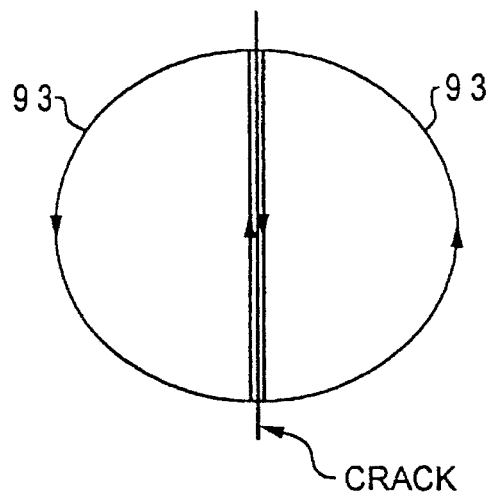
Figure 7C:
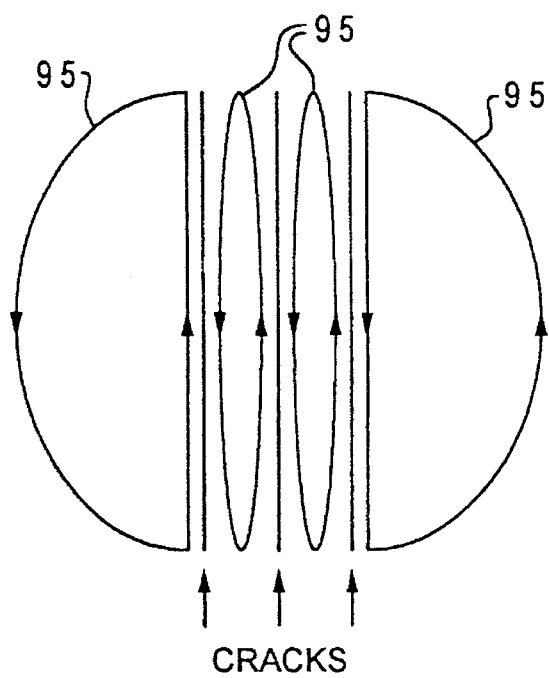

It is believed that the presence of cracks disrupts the diffusion of eddy currents into the wall. Referring to FIG. 7a through FIG. 7c, when the eddy currents do not encounter any cracks, eddy currents 91 are induced into the pipe wall in a somewhat circular pattern (see FIG. 7a) and a normal wall thickness is measured. When a single straight crack is encountered (see FIG. 7b), the circular eddy currents split into two loops 93 in order to maintain a constant magnetic moment. The current of each loop traverses the sides of the crack in opposite directions. The net magnetic field of the dual eddy current loops is the same as if the crack was not present, making detection of the single crack difficult. The eddy currents decay at a rate that is nearly identical to the decay of no crack eddy currents.

However, when plural cracks are present (see FIG. 7c), plural eddy current loops 95 are generated. If the spacing between the cracks is small, the eddy currents die out more rapidly than do no-crack eddy currents. This rapid decay allows the detection of the cracks which are detected as a thinner wall.

The method of the present invention can be combined with another testing technique in order to provide information on the condition of the pipe wall. For example, the method can be used in conjunction with magnetic flux leakage techniques. Magnetic flux leakage techniques use large permanent magnets to induce magnetic flux into pipe walls. Magnetic flux leakage techniques are able to detect wall loss, but are unable to detect cracks.

The use of the method of the present invention in accordance with magnetic flux leakage techniques is in a sense synergistic. By using magnetic flux leakage techniques in combination with the method of the present invention, cracks, and especially stress corrosion cracking, can be identified by correlating the two sets of data. For example, if a wall loss signature is obtained with the method of the present invention, then magnetic flux leakage techniques can be used to determine if wall loss has indeed occurred in the affected wall portion. If magnetic flux techniques detect no wall loss, then an inference can be made that the anomaly detected by the method of the present invention represents cracks.

Magnetic flux leakage requires the use of a magnet to provide a magnetic flux for the pipe wall. The method of the present invention also uses a magnet in order to speed inspection. Thus, much of the hardware used for testing can be shared by both magnetic flux leakage techniques and the method of the present invention. For example, referring to FIG. 1, the magnet 53 can be used to simultaneously provide a magnetic field in the pipe wall for both techniques. A second set of sensing heads 27A are provided to sense the magnetic flux leakage in the pipe. The sensing heads each contain one or more induction coils 31M. The induction coils can be the type shown in FIG. 4. The induction coils 31M are connected to the receiver 73 (see FIG. 5).

When the pipe wall is magnetized by the magnet 53, magnetic lines of flux flow through the wall. If the pipe wall is disrupted by a defect, such as wall loss, then its permeability is changed and some of the flux will leak from the discontinuity. By measuring the intensity of the leakage flux, the severity of the defect can be determined. One type of magnetic flux leakage is described in Schubel, U.S. Pat. No. 4,445,088, the disclosure of which is incorporated herein by reference.

Although the present invention has been described as being used in conjunction with moving transmitting and receiving sensors, the sensors could also be stationary during the inspection process. Also, the present invention need not be used in conjunction with a steady-state magnet 53.

Various antenna configurations can be used in addition to the configurations described above. For example, a receiving antenna could be enlarged so as to cover a larger area. This would be particularly useful when the transmitting and receiving antennas are moving during data acquisition. The receiving antenna could be elongated in the direction of travel to form an ellipse, although a longer receiving antenna will reduce the spatial resolution. The transmitting antenna would be located at the forward end of the receiving antenna. As the antenna is moved along the pipe wall, the transmitting antenna would induce eddy current into the pipe wall. The decay of the induced currents could initially be detected by the forward portion of the receiving antenna, as that is the portion of the receiving antenna that is located adjacent to the portion of the wall that has the eddy currents present therein. As the antennas move forward, the eddy currents will decay and the middle and rear portions of the receiving antenna will be located adjacent to the portion of the wall that contains the decaying eddy currents. Thus, the decaying eddy currents can be detected.

The foregoing disclosure and the showings made in the drawings are merely illustrative of the principles of this invention and are not to be interpreted in a limiting sense.

We claim:

1. A method of detecting cracks in an electrically conductive object, comprising the steps of:

a) inducing an eddy current into a portion of said object with an abruptly changing magnetic field;

b) while said induced eddy current decays in said object portion, detecting the decay of said induced eddy current;

c) determining if a family of cracks is present in said object portion from said detected decay.

2. The method of claim 1 wherein, the step of determining if a family of cracks is present in said object portion from said detected decay further comprises the step of distinguishing between a family or cracks in said object portion and a reduction in thickness of said object portion by determining the magnetic flux leakage of said object portion.

3. The method of claim 2 wherein said step of distinguishing between a family of cracks in said object portion and a reduction in thickness of said object portion further comprises the step of determining if the magnetic flux leakage of said object portion indicates a reduction in thickness of said object portion.

4. The method of claim 2 further comprising the step of subjecting said object portion to a steady-state magnetic field during said step of inducing an eddy current into said object portion.

5. The method of claim 4 further comprising the step of locating a transmitting antenna and a receiving antenna in proximity to said object portion so as to induce an eddy current and detect said induced eddy current.

6. The method of claim 1 further comprising the step of locating a transmitting antenna and a receiving antenna in proximity to said object portion so as to induce an eddy current and detect said induced eddy current.

\* \* \* \* \*